(12) United States Patent
Siedenburg et al.

(10) Patent No.: US 11,013,488 B2
(45) Date of Patent: May 25, 2021

(54) PATIENT MONITORING AND TREATMENT SYSTEMS AND METHODS

(71) Applicant: Stryker Corporation, Kalamazoo, MI (US)

(72) Inventors: Clinton T. Siedenburg, Everett, WA (US); Arthur T. Lounsbery, Woodinville, WA (US); Mitchell A. Smith, Sammamish, WA (US); Robert G. Walker, Seattle, WA (US)

(73) Assignee: Stryker Corporation, Kalamazoo, MI (US)

(*) Notice: Subject to any disclaimer, the term of this patent is extended or adjusted under 35 U.S.C. 154(b) by 66 days.

(21) Appl. No.: 16/013,484

(22) Filed: Jun. 20, 2018

(65) Prior Publication Data

US 2018/0369065 A1 Dec. 27, 2018

Related U.S. Application Data

(60) Provisional application No. 62/524,088, filed on Jun. 23, 2017.

(51) Int. Cl.
*A61B 5/00* (2006.01)
*A61B 8/04* (2006.01)
(Continued)

(52) U.S. Cl.
CPC .............. *A61B 8/04* (2013.01); *A61B 5/0022* (2013.01); *A61B 5/0059* (2013.01);
(Continued)

(58) Field of Classification Search
CPC ....... A61B 8/04; A61B 8/5223; A61B 8/4236; A61B 5/14551; A61B 5/0452; A61B 5/0205; A61B 5/02028; A61B 5/0059; A61B 5/0064; A61B 5/0022; A61B 5/6833; A61B 5/02108; A61B 8/06; A61B 8/4416; A61B 5/08; A61B 5/029; A61B 5/02125; A61B 5/02007; A61B 5/0531; A61B 2560/0214; A61B 2560/0252; A61B 5/0836; A61B 5/14552; A61B 5/0245; A61B 2562/242; A61B 8/488; A61H 31/005; A61H 2201/5097; A61H 2201/5084; A61H 2201/168;
(Continued)

(56) References Cited

U.S. PATENT DOCUMENTS

| 5,535,747 A * | 7/1996 | Katakura | A61B 8/04 600/438 |
| 2006/0211942 A1* | 9/2006 | Hoctor | A61B 8/4236 600/438 |

(Continued)

*Primary Examiner* — Rex R Holmes
(74) *Attorney, Agent, or Firm* — Lee & Hayes, P.C.

(57) ABSTRACT

Non-invasive blood pressure (NIBP) systems and methods are disclosed that measure a blood pressure, and in some examples a beat-to-beat blood pressure, of a patient without restricting blood flow. The NIBP systems determine an efficacy of administered cardiopulmonary resuscitation (CPR) to the patient based on the measured blood pressure and are able to optionally output the CPR efficacy or generate user prompts based on the CPR efficacy. Further, the disclosed NIBP systems can generate user instructions to administer further treatment to the patient based on the CPR efficacy.

24 Claims, 5 Drawing Sheets

(51) Int. Cl.
    *A61B 5/021*     (2006.01)
    *A61B 5/349*     (2021.01)
    *A61B 5/02*     (2006.01)
    *A61B 5/0205*     (2006.01)
    *A61B 5/1455*     (2006.01)
    *A61B 8/00*     (2006.01)
    *A61B 8/08*     (2006.01)
    *A61H 31/00*     (2006.01)
    *A61B 5/0245*     (2006.01)
    *A61B 5/083*     (2006.01)
    *A61B 5/0531*     (2021.01)
    *A61B 8/06*     (2006.01)
    *A61B 5/029*     (2006.01)
    *A61B 5/08*     (2006.01)

(52) U.S. Cl.
    CPC .......... *A61B 5/0064* (2013.01); *A61B 5/0205* (2013.01); *A61B 5/02028* (2013.01); *A61B 5/02108* (2013.01); *A61B 5/14551* (2013.01); *A61B 5/349* (2021.01); *A61B 5/6833* (2013.01); *A61B 8/4236* (2013.01); *A61B 8/5223* (2013.01); *A61H 31/005* (2013.01); *A61B 5/02007* (2013.01); *A61B 5/029* (2013.01); *A61B 5/0245* (2013.01); *A61B 5/02125* (2013.01); *A61B 5/0531* (2013.01); *A61B 5/08* (2013.01); *A61B 5/0836* (2013.01); *A61B 5/14552* (2013.01); *A61B 8/06* (2013.01); *A61B 8/4416* (2013.01); *A61B 8/488* (2013.01); *A61B 2560/0214* (2013.01); *A61B 2560/0252* (2013.01); *A61B 2562/242* (2013.01); *A61H 2201/165* (2013.01); *A61H 2201/168* (2013.01); *A61H 2201/5043* (2013.01); *A61H 2201/5058* (2013.01); *A61H 2201/5082* (2013.01); *A61H 2201/5084* (2013.01); *A61H 2201/5097* (2013.01); *A61H 2230/045* (2013.01); *A61H 2230/208* (2013.01); *A61H 2230/255* (2013.01); *A61H 2230/405* (2013.01)

(58) Field of Classification Search
    CPC .... A61H 2201/5043; A61H 2201/5082; A61H 2201/165; A61H 2201/5058; A61H 2230/405; A61H 2230/255; A61H 2230/208; A61H 2230/045
    See application file for complete search history.

(56) References Cited

U.S. PATENT DOCUMENTS

| | | | |
|---|---|---|---|
| 2010/0022886 A1* | 1/2010 | Ayati | A61B 5/6822 600/454 |
| 2016/0199251 A1* | 7/2016 | Aelen | A61H 31/005 601/41 |
| 2017/0000688 A1* | 1/2017 | Kaufman | A61H 31/005 |
| 2018/0199834 A1* | 7/2018 | Siedenburg | A61B 5/0295 |
| 2018/0235567 A1* | 8/2018 | Bezemer | A61B 5/02125 |

* cited by examiner

PATIENT MONITORING AND TREATMENT SYSTEMS AND METHODS

CROSS-REFERENCE TO RELATED APPLICATIONS

This patent application claims the benefit of and priority to U.S. Provisional Patent Application Ser. No. 62/524,088, filed on Jun. 23, 2017, entitled "Noninvasive Blood Pressure (NIBP) Pulse Wave Velocity (PWV) by Ultrasound Sensor," the contents of which are hereby incorporated by reference in their entirety.

BACKGROUND

Patient monitoring and treatment can involve invasive means that require inserting sensors within a patient to acquire the requisite data, such as a blood pressure of the patient. The blood pressure of a patient is a critical measurement that is used in monitoring and treating the patient. There are two means by which the blood pressure of the patient can be measured, one is invasive and the other is non-invasive. In the invasive means, the blood pressure is obtained by direct measurement, requiring a sensor to be inserted into the circulatory system of the patient to obtain the measurements. In certain situations that require precise, beat-to-beat blood pressure measurements, such as some surgical applications, the invasive means can provide the necessary data. Further, the invasive means can cause discomfort in the patient or the subject for which the blood pressure is being measured. Additionally, there is an increased risk of complications and/or increased expense due to the invasive nature of such blood pressure measurement.

In the non-invasive means, the sensing of the blood pressure is done externally to the patient and tends to only capture peak pressure readings, such as an intra-arterial blood pressure at diastole and systole, which provides little to no information about the patient's blood flow or vessel health. Typically, this involves the application of a cuff about a limb of the patient and the pressurization of the cuff to cut-off circulation through the limb. The pressure applied by the cuff to the limb is slowly reduced and as blood flow is resumed, the blood pressure can be measured based on the pressure remaining in the cuff. This process is often repeated multiple times to ensure an accurate measurement or as a means of monitoring over an extended period of time, with pauses required between measurement instances. While this means is non-invasive, it does require the temporary restriction of circulation in a portion of the patient, which can be damaging to the health of the patient and also requires time for the process to be fully performed. Additionally, such non-invasive blood pressure measurement techniques are sensitive to motion of the patient, accessories to the non-invasive blood pressure equipment being bumped or jostled during patient care or transport, etc., which can result in inaccurate and/or unobtainable blood pressure measurements. In patient transport or emergency situations, the patient and the equipment, such as the hosing, can be subjected to a large amount of motion during time in which an accurate blood pressure measurement can be critical to assess the state of the patient.

As such, there is a need for non-invasive patient monitoring and treatment systems and methods that can provide accurate patient information, such as blood pressure, for use in monitoring and/or treating the patient.

DETAILED DESCRIPTION

Non-invasive patient monitoring and treatment systems and methods are described herein. Non-invasive blood pressure (NIBP) measurement systems and/or methods can calculate a blood pressure and/or vessel dynamics of a person. Such data can be used in the monitoring and/or treatment of the person, such as for clinically evaluating a condition, or state, of the person. Additionally, the collected data can be correlated and/or aggregated with other physiological parameter data and/or vital signs of the person. Correlated and/or NIBP data can provide indications of the effectiveness of a treatment of the person, can provide indications of potential changes in the clinical condition/state of the person and/or can provide data to assist with monitoring the clinical condition/state of the person or a change and/or addition in care and/or treatment to be provided to the patient. In an example, the NIBP and/or correlated data can provide indications of the effectiveness of cardiopulmonary resuscitation administration and can also be used to provide feedback to modify or alter the administration of cardiopulmonary resuscitation to improve its effectiveness. Further, conditions and/or ailments of the person can be tracked, or monitored, using the NIBP and/or other physiological and/or vital signs data.

The NIBP data can be collected with the assistance of an NIBP device. The NIBP device can radiate energy into tissues of the person. The radiated energy can reflect from one or more of the tissues, such as flowing blood, and the reflected energy can be detected, or sensed, by a sensor to generate an NIBP signal. The NIBP signal can be processed to calculate the blood pressure and/or vessel dynamics of the person. Additionally, the NIBP device can receive and/or process other vital signs data of the person to assist with monitoring and/or treatment of the person.

Figure 1:
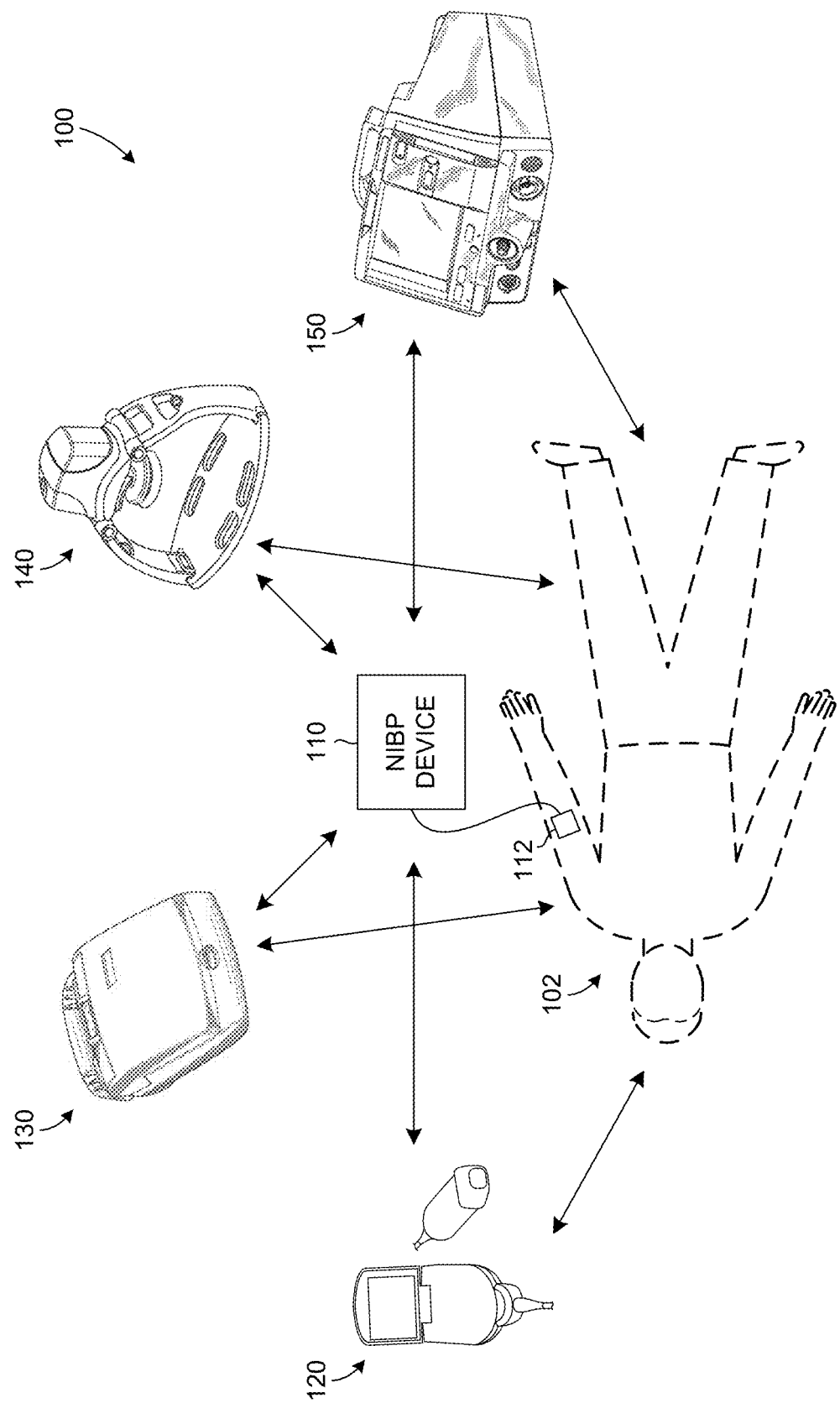
FIG. 1 is an example patient monitoring and/or treatment system.

FIG. 1 illustrates an example patient monitoring and/or treatment system 100. One or more medical devices can be used to monitor and/or treat a patient 102, such as a non-invasive blood pressure (NIBP) device 110, an ultrasound device 120, an automated external defibrillator 130, a chest compression machine (CCM) 140, a monitor/defibrillator 150, and/or other medical, or other, devices/systems. Data, such as patient vital signs data, acquired/sensed by one of the medical devices can be shared amongst the other devices to assist with the monitoring and/or treatment of the patient 102.

The NIBP device 110 can include an NIBP sensor 112 that can be placed on the patient 102 to generate an NIBP signal, or data, that can be processed by the NIBP device 110 to determine a blood pressure of the patient. The NIBP sensor 112 can radiate energy, such as ultrasound or light, into the tissues of the patient to sense and generate the NIBP signal in response to the reflection of the radiated energy from the tissues of the patient, such as flowing blood. The NIBP device 110 can receive the NIBP signal and determine an instantaneous blood velocity that can be used, with a blood density, pulse wave velocity, and/or other vital signs data, to calculate the blood pressure of the patient 102 and/or one or more vessel dynamics of the patient 102.

The data, such as the calculated blood pressure and/or vessel dynamics, can be communicated by the NIBP device 110 to one or more other devices to assist with monitoring and/or treating the patient 102. For example, the NIBP device 110 can share blood pressure, vessel dynamics and/or other data with an automatic external defibrillator (AED) 130, a chest compression machine (CCM) 140, monitor/defibrillator 150 and/or other devices/systems to assist with one or more patient monitoring and/or treatment tasks, such as patient resuscitation. These other devices can alter their patient monitoring and/or treatment in response to and/or based on the data received from the NIBP device 110.

In another example, one of the other devices/systems, such as the ultrasound device 120 and/or the monitor/defibrillator 150, can radiate energy into the tissues of the patient 102 and the reflected energy therefrom can be detected by a sensor of the NIBP device 110 that is placed on the patient 102. The reflected energy can be sensed by the sensor to generate the NIBP signal that can be processed by the NIBP device 110 to calculate a blood pressure and/or vessel dynamics of the patient 102. Alternatively, or additionally, the functionality and/or features of the NIBP device 110 can be integrated with one or more of the other devices/systems used to monitor and/or treat the patient 102. In such an integration, the NIBP functionality can use, or sense, energy normally radiated into patient tissues by the other device/system to generate the NIBP signal/data.

For example, the NIBP device 110 can be integrated with a standard ultrasound machine. For the integration to function properly, a software update may be needed to configure the standard ultrasound machine to further process the raw NIBP data measured by the NIBP device. The existing hardware and/or software of the standard ultrasound machine, such as the transducers, acquisition sequence, and data processing, can be programmed to become the NIBP device without additional hardware being added. Alternatively, emitter/detector combination hardware of the NIBP device could be added to the standard ultrasound machine, for example, in place of or in addition to the machine's existing scan head. The substitute or replacement emitter/detector combination hardware could be electronically coupled to the transmitter and receiver electronics and processing resources of the standard ultrasound machine. Still further, the NIBP device could also transmit its data, in raw waveform or processed in some form, to the standard ultrasound machine to further process and/or display the resulting NIBP measurements and/or NIBP or other physiological parameter data.

The software update on the standard ultrasound machine can be made to existing equipment so that it functions in the integrated fashion when a NIBP device is connected or discovered. The software update to the standard ultrasound machine can include configuring the standard ultrasound machine to perform such functions as calculating the blood pressure and/or vessel dynamics of the patient from the data provided by the NIBP device, for example, and to operate in a different mode for obtaining the image through ultrasound techniques because the imaging processing required can be different when measuring NIBP using the disclosed techniques than for medical ultrasound imaging typically performed with a standard ultrasound machine. The standard ultrasound machine can be updated in any suitable manner.

In a further example, a single NIBP 110 device can be connected, wired and/or wirelessly, to multiple NIBP sensors 112 placed on one or more patients. The NIBP device 110 can monitor/calculate the blood pressure and/or vessel dynamics of the one or more patients upon which the NIBP sensors 112 are placed. Such an arrangement can assist in mass casualty situations wherein a single NIBP device 110 can monitor multiple patients.

Figure 2:
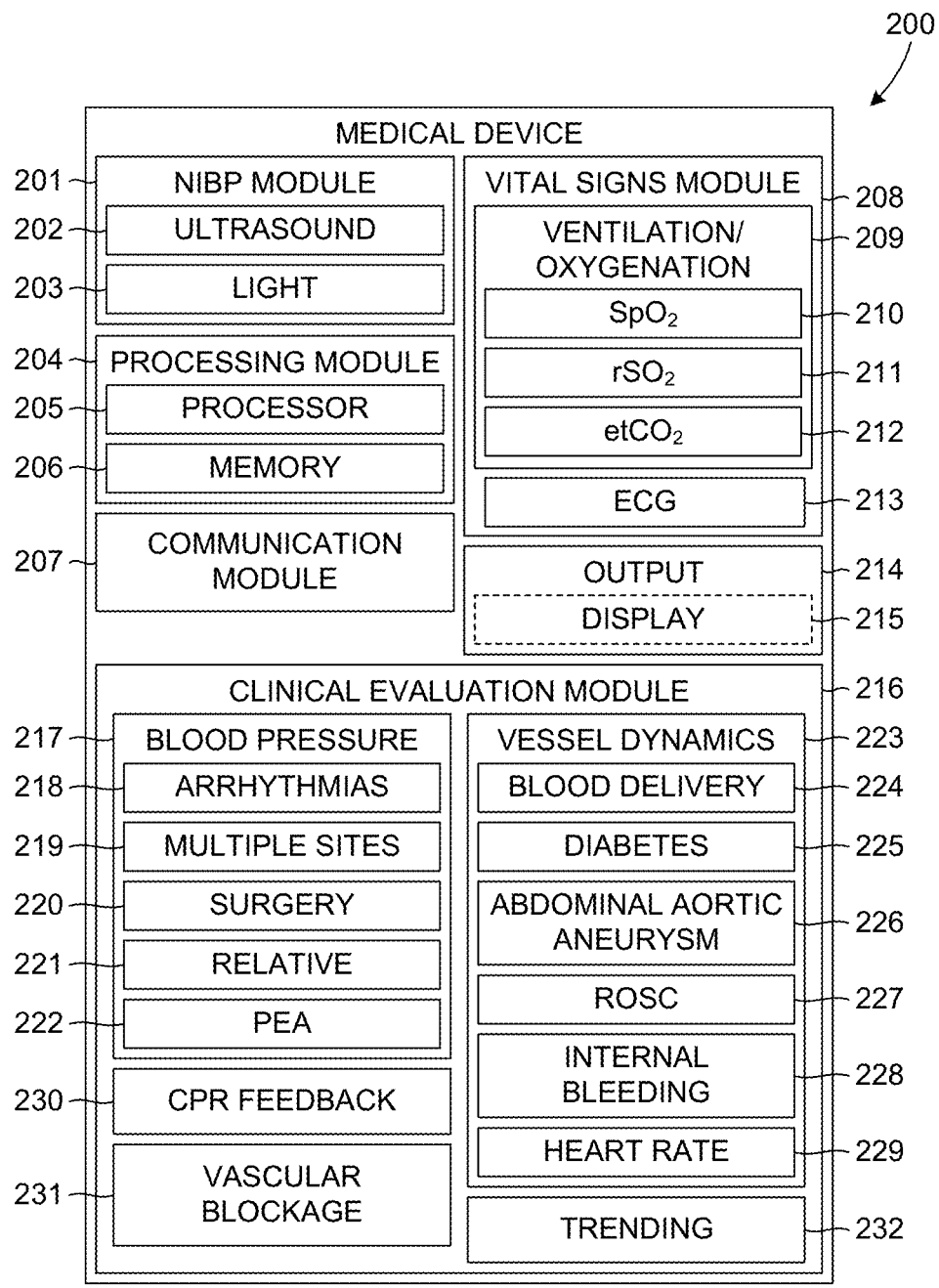
FIG. 2 is a block diagram of an example non-invasive blood pressure (NIBP) device.

FIG. 2 illustrates an example non-invasive blood pressure (NIBP) device 200 that can assist with monitoring and/or treating a patient. The NIBP device 200 can be placed on and/or coupled to a patient, to sense and/or receive vital signs data therefrom, and/or can otherwise receive patient vital signs data and/or any other patient physiological data, to calculate a blood pressure 217 and/or vessel dynamics 223 of the patient. The blood pressure 217, vessel dynamics 223 and/or other vital signs data can assist with evaluating a clinical state of the patient.

An NIBP module 201 of the NIBP device 200 can receive reflected energy, and/or a signal representative thereof, caused by energy, such as ultrasound 202 and/or light 203, radiated and/or transmitted into the tissues of the patient. The NIBP module can process the reflected energy and/or signal to determine a blood velocity and/or pulse wave velocity, which can be used to calculate the blood pressure 217 and/or vessel dynamics 223 of the patient. The NIBP module, and/or an NIBP sensor, can include energy emitters to emit/radiate energy into the tissues of the patient and can include sensors to sense/receive/detect reflected energy. The sensors can generate an NIBP signal that can then be processed by the NIBP module 201 to determine an instantaneous blood velocity, which can be used to calculate the blood pressure and/or vessel dynamics of the patient.

A processing module 204 can control various functions and/or features of the NIBP device 200 and/or can analyze/process data. The processing module 204 can include a processor 205 and memory 206 for storing data and/or instructions for execution by the processor 205. In an example, processing of the NIBP signal can be performed by the processing module 204 to calculate the blood pressure and/or vessel dynamics of the patient. Additionally, the processing module 204 can process other physiological data, such as from a vital signs module 208 and/or other devices/systems, to assist with evaluating a clinical state of the patient.

A communication module 207 can transmit data from and/or receive data to the NIBP device 200 using one or more communication protocols. Communication to/from the NIBP device 200 can be with another device and/or system, such as a patient monitoring and/or treatment device/system. The communication module 207 can transmit data widely, such as via a network and/or the Internet, and/or locally, such as via a Bluetooth, near field communication (NFC), Wi-Fi Direct®, WiGig, cellular, and/or another local network. Additionally, transmissions to/from the communication module 207 can be via a wired and/or a wireless connection.

The vital signs module 208 can receive patient vital signs data from one or more vital signs or other physiological sensors and/or devices/systems and/or can include one or more sensors to sense one or more vital signs or other physiological parameters of the patient. Any patient parameters can be measured, including vital sign(s) and/or any patient physiological parameters. The vital signs and/or patient physiological parameters described in this disclosure include any medical data relating to the patient. FIG. 2 shows a vital signs module 208 by way of example, and the vital signs module 208 could alternatively be identified as a patient physiological parameters module or other patient data module. The vital signs monitored by the vital signs module 208 can include ventilation/oxygenation 209 and/or ECG 213 parameters. The ventilation/oxygenation 209 can include pulse oximetry 210, tissue/regional oximetry 211 and/or end-tidal $CO_2$ 212 data. The vital signs data of the vital signs module 208 can be used with the NIBP data to assist with evaluating a clinical state of the patient, such as by a clinical evaluation module 216.

The NIBP device 200 can include an output 214 that can output the blood pressure, vessel dynamics, vital signs and/or physiological parameters, clinical evaluation/clinical state, and/or other data to a user, device and/or system. The user, device and/or system can receive the data from the output to assist with monitoring and/or treating the patient. Optionally, the output 214 can include a display 215 that can display and/or present the data to a user, such as to assist with monitoring and/or treatment of the patient by the user. Other output can also be included such as haptic, auditory, and visual output, for example.

The clinical evaluation module 216 can evaluate a clinical state/condition of the patient based on the NIBP, vital signs and/or other data. One or more clinical states/conditions can be evaluated based on the blood pressure data and other can be based on the vessel dynamics data. Additionally, the clinical evaluation module 216 can provide CPR feedback 230, vascular blockage 231 data, trends 232 and/or other data, based on the NIBP, vital signs and/or other data.

The clinical evaluation module 216 can use blood pressure 217 data to evaluate clinical states/conditions, such as arrhythmias 218, to monitor blood pressure at multiple sites 219 of the patient, monitor blood pressure during surgery 220, monitor relative blood pressure 221, detect pulseless electrical activity (PEA) and/or other states/conditions. The blood pressure 217 monitoring can be continuous, allowing the blood pressure to be monitored throughout the cardiac cycle and beat-to-beat. Rather than typical peak systolic and/or diastolic values, the blood pressure can be monitored on a finer/more granular scale throughout the duration of each cardiac cycle or selected sampling of cardiac cycles. Additionally, or alternatively, the blood pressure can be monitored for an interval(s) and/or monitored spaced apart by an interval(s), allowing for the patient's blood pressure to be monitored over an extended period of time.

To detect/evaluate the patient for arrhythmias 218, the clinical evaluation module 216 can evaluate the continuous blood pressure measurement. Evaluation of the arrhythmia(s) 218 can include characterizing the arrhythmia 218 and/or estimating a severity of the arrhythmia 218. The arrhythmia 218 detection/evaluation can be used by a user, device and/or system to assist with further patient care, such as monitoring/treatment decisions. Additionally, the information can be used to evaluate patients with syncope, such as neurocardiogenic syncope, which can be caused by atrial fibrillation, ventricular fibrillation and/or other arrhythmias. Further, other types of syncope can also be detected and/or evaluated by the clinical evaluation module 216.

Blood pressure of the patient can be monitored simultaneously at multiple sites 218 across the patient's body, allowing for total blood supply to be monitored, evaluated and/or controlled. Multi-site 218 monitoring of blood pressure can be used to monitor a patient during surgery 220 or in an intensive care unit, for example. Some surgeries, such as open heart surgery, can require invasive blood pressure monitoring across one or more sites of the patient's body, which one or more of the disclosed NIBP devices 200 can replace. NIBP sensors and/or devices can be placed at multiple locations of the patient's body to obtain the whole body blood pressure measurement. In the example of multiple NIBP sensors, each sensor can communicate wirelessly to a common NIBP device which can process the received NIBP signals to provide the whole body blood pressure data. The wireless communication can reduce the intrusion of cables within the surgical area. In other surgeries, localized monitoring of the blood pressure around the surgical area can be required and/or desired. Multiple NIBP sensors and/or devices can assist with monitoring the local blood pressure about the surgical area. In the open heart surgery example, the NIBP sensor(s) and/or device can be integrated with one or more surgical tools to monitor blood pressure in various areas of the heart.

Relative 221 blood pressure can also be monitored by the clinical evaluation module 216. Relative changes in blood pressure can be monitored and can trigger alerts when the relative change is outside of a threshold value/range. In an example, changes in pulse pressure can trigger alerts when the difference in systolic and diastolic pressures are too small, too large and/or too varying.

Pulseless electrical activity (PEA) 222 can also be detected based on the blood pressure data and the ECG data 213. The lack of blood pressure combined with ECG data indicating electrical activity can identify the presence of PEA 222.

The clinical evaluation module 216 can use vessel dynamics 223 to assist with evaluating a clinical state/condition of the patient. Blood delivery 224, diabetes 225, abdominal aortic aneurysm 226, Return of Spontaneous Circulation (ROSC) 227, internal bleeding 228, heart rate 229 and/or other clinical states and/or conditions can be evaluated using vessel dynamics 223 data, such as calculated from the NIBP module 201.

Blood delivery 224 can be monitored and/or evaluated by the clinical evaluation module 216. The NIBP module 201 can determine various vessel dynamics, such as blood flow velocity and vessel diameter, which can be used to determine a blood rate and blood delivery volume. Using the blood rate and delivery flow, a low blood flow condition can be identified and/or characterized, such as scored for its severity and/or impact on the patient's physiological state. This information can assist a user, device and/or system with patient monitoring and/or treatment. In some examples, the low blood flow condition and/or the severity score are output to a user in the form of a user prompt or a visual, haptic, or audible alert or indicator. The processing module can determine recommended treatments for the patient based on the low blood flow condition and/or the severity score, which can also be output to the user in any desired form.

The blood delivery 224 can be measured locally on a patient, such as at patient extremities. Additionally, the blood delivery 224 data can assist with identifying/monitoring diabetes 225. Diabetics often suffer from low blood flow to extremities, which can be monitored by the clinical evaluation module 216 to assist with determining/measuring an effectiveness of treatment and/or assessing the potential need for surgery. The NIBP device 200 and/or monitoring can be used for out-patient and/or at-home patient monitoring to assist with monitoring the diabetic conditions, trends of the condition and/or evaluating the treatment therapy effectiveness. The blood delivery 224 monitoring can be controlled to occur, and/or increase monitoring, at required, and/or desired, times, such as during critical times and not occur, and/or decrease monitoring, during non-critical times.

An abdominal aortic aneurysm 226 can be identified and/or monitored by the clinical evaluation module 216. In an example, the NIBP module 201 can use ultrasound 202, which can also be used to image the aorta to assist with diagnosing and/or monitoring the aneurysm 226. Additionally, the vessel dynamics 223 can include measurements of the vessel which can also assist with identifying and/or monitoring the aneurysm 226. Further, local blood pressure 217 measurements can also assist with identifying and/or monitoring the aneurysm 226.

The clinical evaluation module 216 can also detect/identify the Return of Spontaneous Circulation (ROSC) 227 using the vessel dynamics 223 data. For example, the vessel dynamics 223 data can indicate blood flow, such as ROSC, which can be communicated to a user, device and/or system to assist with defibrillation shock administration decisions.

Internal bleeding 228 can also be identified, monitored and/or characterized using ultrasound 202. The ultrasound 202 can be used to detect internal bleeding 228 when placed over areas of the body where blood collects during internal bleeding 228. Further, the ultrasound 202 can be placed over trauma sites to identify the presence of ruptured vessels.

The clinical evaluation module 216 can also determine a heart rate 229 based on the NIBP, vital signs and/or other data, such as the vessel dynamics 223 data. The heart rate 229 can be displayed as a value and/or classification and can assist a user, device and/or system with patient monitoring and/or treatment.

The clinical evaluation module 216 can also provide cardiopulmonary resuscitation (CPR) feedback 230. The clinical evaluation module 216 can use NIBP data, such as from the NIBP module 201, and optionally vital signs data, such as from the vital signs module 208, to provide a measure of the efficacy of the applied CPR. For example, ventilation/oxygenation 209 data can be used to assess the efficacy of administered ventilations (both mechanically and manually administered) and can be measured by end tidal $CO_2$ (et$CO_2$) data. ECG 213 data and blood pressure data can be used to identify potential hemodynamic collapse and, optionally, generate an alert to a user. The vital signs data, such as ventilation/oxygenation 209 and/or ECG 213 data, and blood delivery 224 data can be quantified to provide a measurement of the efficacy of CPR being applied to a patient. A user, device and/or system can alter one or more characteristics of the CPR in response to the CPR feedback 230 provided by the NIBP device 200. For example, chest compression depth and/or rate and compression element position (i.e., hand position for manual CPR or piston position for mechanical CPR) can be altered in response to the CPR feedback 230. Further, the clinical evaluation module 216 can generate a user instruction or prompt to administer treatment to the patient based on the CPR feedback 230. The treatment can be continued CPR, defibrillation therapy, administration of medication, ventilation (mechanical and/or manual) or intubation procedures, etc.

Vascular blockage 231 can also be identified by the clinical evaluation module 216. The NIBP data can be evaluated to identify blockages, such as by ultrasound 202, and/or identify turbulent flow which can be indicative of blockages. The identification and/or monitoring of vascular blockage 231 can assist with monitoring and/or treatment of the patient.

The clinical evaluation module 216 can also monitor the NIBP, vital signs and/or other data for trends 232. The data can be aggregated over time to identify trends 232, which can assist with predicting a future physiological/clinical state/condition of the patient. The trending 232 data can be plotted, extrapolated and/or displayed to provide a user, device and/or system with data to assist with patient monitoring and/or treatment. Further, the extrapolation of the data can provide a prediction that one or more vital signs and/or conditions may potentially cross a threshold value, which can allow a user, device and/or system to take preventative, or proactive, action, such as patient treatment.

To assist with increasing the accuracy of the NIBP device 200, a user, device and/or system can provide various data. For example, the NIBP module 201 can use a fixed, or assumed, blood density in calculating the blood pressure of the patient. However, a patient can have a non-standard blood density, such as due to transfusions, infection, disease, or other factors, which can alter the overall density of the patient's blood. A user, device and/or system can provide an input to the NIBP device 200 that is indicative of the altered blood density to cause the NIBP device 200 to compensate for the altered blood density in calculating the blood pressure and/or vessel dynamics. Additionally, ultrasound contrast agents can be used to assist with the signal-to-noise ratio of detecting/monitoring the blood flow of the patient. The contrast agents can assist with increasing the accuracy and/or detectability of blood flow in areas of the patient's body in which it can otherwise be difficult to detect using ultrasound without contrast agents. Another method of increasing accuracy can include extending intervals of monitoring to reduce variations in the measurements that can be introduced due to noise. For example, the measurement data can be gathered over a period of time and averaged, and/or otherwise statistically manipulated, to improve the signal-to-noise ratio of the measured data.

Calibration can also be used to assist with increasing the accuracy of the NIBP device 200. For example, an automated or manual blood pressure measurement can be made and compared to the blood pressure measurement calculated by the NIBP device 200. The NIBP device 200 can then be calibrated and/or adjusted based on the automated or manual blood pressure measurement.

Calibration can also be implemented when using one or more NIBP devices 200 to measure blood pressure at multiple sites on the patient. For example, a reference NIBP calculation at a central location on the patient can be used to calibrate the NIBP calculation at a second location on the patient based on the separation and/or position of the central and second locations.

Figure 3:
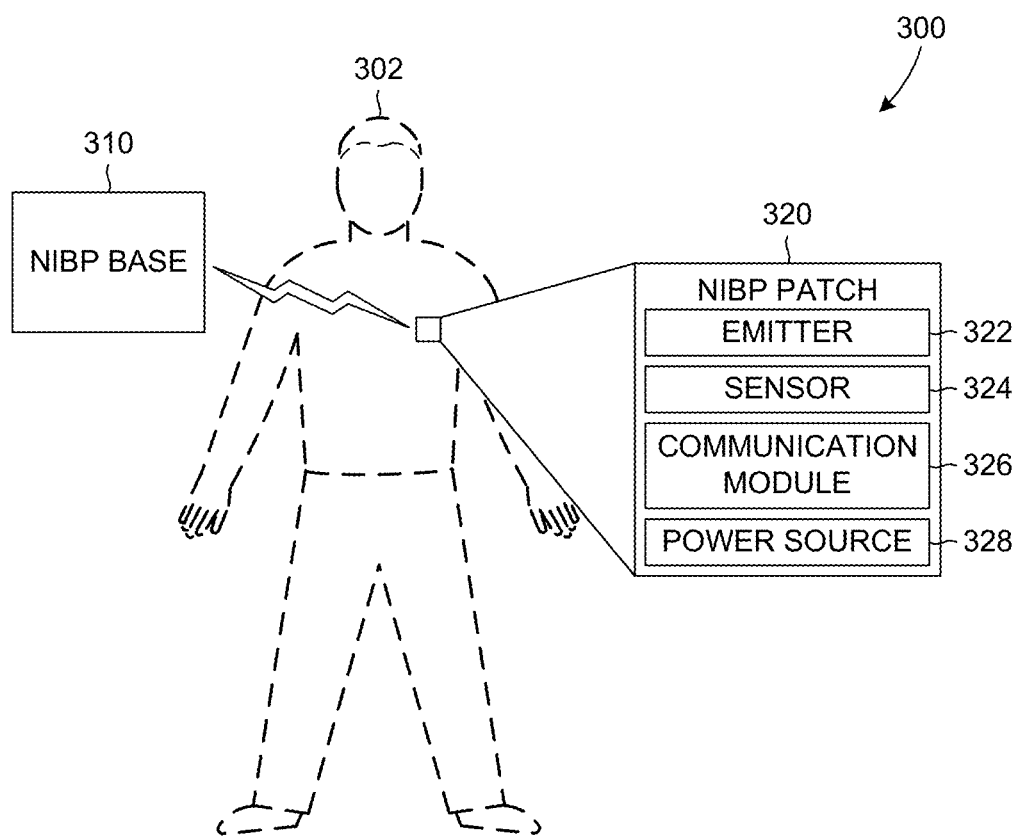
FIG. 3 is an example NIBP patch system.

FIG. 3 illustrates an example non-invasive blood pressure (NIBP) patch system 300 that includes an NIBP patch 320 that communicates with an NIBP base 310. The NIBP patch 320 is placed on a patient 302 and transmits an NIBP signal, or data, to the NIBP base 310. The NIBP base 310 can process the received NIBP signal to calculate a blood pressure and/or vessel dynamics of the patient 302.

The NIBP patch 320 can be releasably attached to the patient 302, such as by an adhesive, and can be worn by the patient for a period of time. In an example, a user can apply the NIBP patch 320 to the patient 302 to monitor the blood pressure, vessel dynamics and/or patient monitoring/treatment characteristics, with the NIBP base 310. In another example, the NIBP patch 320 can be applied to the patient 302 to collect patient data for an interval and/or spaced apart intervals, to collect various patient vital signs data over a period of time. The NIBP patch 320 can be disposable after a particular number of uses or type of use. For example, the NIBP patch could be disposable after being used a desired number of times on a single patient or on multiple patients.

The NIBP patch is small in size and communicates wirelessly with its other system components, and, in some examples, it communicates with the processing circuitry that is physically located on another component with which the NIBP patch is configured to communicate wirelessly. In another example, the NIBP patch is used during a particular use, such as a surgery or a trauma event and is intended for a single use based on the type of application in which it is being used.

Alternatively, the NIBP device could be implanted into a patient as a permanent monitoring device at a specific site in the body. Because of its small size and wirelessly capabilities, the implantable NIBP device could communicate wirelessly with other system components and/or could be programmed or re-programmed from a remote computing device to measure NIBP for certain conditions and under desired parameters. The implantable NIBP device could be powered by a battery or powered by radio waves, for example.

The NIBP patch 320 includes an emitter 322, a sensor 324, a communication module 326 and a power source 328. The emitter 322 can radiate energy, or waves, such as ultrasonic and/or light energy/waves, into the tissues of the patient 302. The radiated energy reflects from various tissues of the patient 302, such a flowing blood, and the sensor 324 receives the reflected energy. The reception of the reflected energy by the sensor 324 causes an NIBP signal, or data, to be generated.

Generally stated, the disclosed NIBP patch measures two values which can be used to compute a patient's instantaneous blood pressure. The NIBP patch measures the instantaneous non-invasive blood pressure (NIBP) of a patient with an apparatus that determines the values for, in one example, two of the unknowns in the water hammer equation: pulse wave velocity (PWV) and instantaneous blood velocity ($v_i$). The water hammer equation relates instantaneous blood pressure to pulse wave velocity and blood flow as follows:

$$P_i = \rho PWV\, v_i$$

where PWV is the pulse wave velocity, $\rho$ is the density of the blood which may be assumed to be a constant, for example, $v_i$ is the instantaneous velocity of the blood, and $P_i$ is the desired instantaneous blood pressure. Alternative equations relating the pulse wave velocity and blood flow can also be used.

Some conventional NIBP measurement systems rely on PWV to measure NIBP, but each requires an initial calibration measurement, taken at least once, to convert a relative blood pressure value to an actual blood pressure value. The required calibration measurement is typically taken using a traditional blood pressure cuff, for example on the patient's arm or perhaps the leg. Such conventional NIBP measurement systems that require an initial calibration and all calculations are based on a difference or differential value of that initial calibration measurement to achieve an actual measurement.

The disclosed NIBP systems and devices instead take an instantaneous blood pressure measurement rather than a change from an initial calibration measurement. Avoiding the need for a calibration measurement, prevents the patient from experiencing blood flow restriction altogether, which are required by all cuff-based NIBP systems. PWV is highly correlated with blood pressure (BP) so that changes in blood pressure can be calculated from changes in PWV by relying on an initial calibration measurement to produce a relatively accurate blood pressure measurement. The traditional calibration methods require use of a separate, initial calibration value or values to register a particular PWV to a particular value of blood pressure (as opposed to simply a change in blood pressure) for a patient. State of the art of NIBP using PWV typically uses a standard cuff-based measurement, to restrict the blood flow, in order to measure and associate a particular blood pressure to a particular PWV measurement in a patient. Restricting the blood flow requires that the patient's appendage being measured is compressed. Such restriction of the patient's blood flow prevents such conventional methods of measuring blood pressure from being applied to areas of the patient's body that cannot withstand restricted blood flow, such as a patient's neck, for example.

In this way, conventional methods and devices that provide NIBP measurements using PWV require a distinct calibration step. In contrast to the state of the art, the disclosed embodiments include a method and device that eliminate the requirement of a distinct calibration step, especially using a technology that temporarily restricts blood flow. In short, the disclosed embodiments include self-calibrating NIBP systems and methods using PWV, or alternatively, NIBP systems and methods using PWV without the temporary restriction of blood flow.

The lack of need for a calibration step for devices using the method taught herein arises from the use of the water hammer equation in its integrated (non-differential) form, for example. In the water hammer equation, the blood pressure is related to the PWV by two scale factors—blood velocity and blood density—that can be known without a distinct calibration step. The scale factors are found using the same ultrasound technology that is used to measure the PWV. Blood velocity is measured according to this disclosure and blood density is assumed based on a known value with or without a correction factor. In this way, a particular blood pressure is calculated as the PWV scaled by the blood density and the blood velocity.

Blood velocity can be acquired using ultrasound as a time varying waveform. PWV can also be measured with ultrasound as a time varying function. The time-varying nature of the PWV means that it can be updated from beat to beat or less frequently, if desired. The time-varying nature of the blood velocity means that blood velocity can be measured at a much finer resolution than at peak systole and diastole values during a cardiac cycle. Instead the blood velocity is measured continuously throughout the duration of the cardiac cycle for as many cardiac cycles as desired. Because blood density is already sufficiently known and is relatively constant, not only can a particular blood pressure measurement be known from the scaled value of the PWV as if it were obtained by a standard cuff-based measurement or even an invasive catheter measurement, but all manners of blood pressure measurements can be made as time-varying waveforms describing the instantaneous pressure at as many points during a cardiac cycle as desired. Blood pressure can be monitored continuously throughout the cardiac cycle with as fine a resolution as is required, and this can be done for as many consecutive or periodic cardiac cycles as is desired for beat-to-beat monitoring, or as intermittently as desired.

Measuring the instantaneous blood pressure instead of its change relative to a calibrated baseline measurement means, for example, that as arterial walls stiffen (due to disease, drug therapy, and/or normal vasculature responses, for example) which increases the PWV, this new PWV value is measured along with any corresponding change in blood velocity to produce an updated blood pressure waveform. Additionally, if the heart pumps more or less energetically, the blood velocity changes accordingly, which results in the blood pressure changing proportionately, all else equal. This updated blood velocity measurement at the prevailing PWV (which characterizes the state of the vasculature) corresponds to the updated blood pressure after being scaled by blood density. In other words, since there are two measurements made, PWV and blood velocity, and not just PWV alone, a distinct calibration step is not needed, as the ambiguity of PWV by itself is remedied by adding the second measured value of blood velocity. This is of great value over conventional patient NIBP monitoring using PWV alone where typically the calibration step requires a blood pressure measurement performed by restricting blood flow, which can be more costly, time consuming, and/or uncomfortable to the patient. Ultrasound or light technology can be used to acquire both the PWV and the blood velocity although other methods of obtaining the PWV and the blood velocity can alternatively or additionally be used. Further embodiments implement various techniques and devices to measure or detect both pulse wave velocity and instantaneous blood velocity.

An NIBP sensor can be attached to a patient, as shown in FIG. 3. As discussed at length above, the sensor includes an ultrasound sensor and may include one or more alternative sensors.

The NIBP sensor substantially simultaneously measures pulse wave velocity and instantaneous blood velocity, as discussed above. Each of those two basic steps may be accomplished in numerous ways. For example, pulse wave velocity may be measured using a sound analysis based on information known about the configuration of the NIBP sensor. In one specific embodiment, the sensor is configured such that an ultrasound waveform radiated by the sensor produces grating lobes having known characteristics, such as a grating lobe separation angle of θ. The sound analysis may further compute a depth from the sensor to a target blood vessel. Based on those data, ultrasound imaging combined with triangulation techniques can be used to compute a rate at which a pulse travels through the vessel, which is the pulse wave velocity of the vessel.

Similarly, instantaneous blood velocity may be measured using Doppler effect techniques. In one specific embodiment, the Doppler analysis can identify the phase change of a returned signal from the blood between each of 10 kHz repetitions, for example.

Once pulse wave velocity and instantaneous blood velocity are known, the instantaneous blood pressure is calculated by using an equation that relates the blood velocity to the PWV, such as the water hammer equation. Based on that equation, pulse wave velocity, instantaneous blood velocity, and blood pressure are related as follows:

$$P_i = \rho PWV\, v_i$$

Once calculated, the blood pressure measurement may be presented to a user for use in treatment of the patient. It should be appreciated that, in another alternative, continuous wave Doppler (CWD) may be used as an alternative to pulse wave Doppler (PWD).

Referring again to FIG. 3, the communication module 326 of the NIBP patch 320 can use one or more communication protocols, such as a network connection, to transmit data from the NIBP patch 320 to the NIBP base 310. In an example, the communication module 326 can communicate with the NIBP base 310 via a Bluetooth®, a near-field communication (NFC) connection, Wi-Fi Direct®, and/or WiGig. Data transmitted by the NIBP patch 320 to the NIBP base 310 can include the NIBP signal.

The power source 328 can include an energy storage device, such as a battery, and can supply the requisite energy to the various components/systems of the NIBP patch 320. The power source 328 can be permanently integrated with the NIBP patch 320, or can be removable/replaceable. Intermittent or modulated data collection by the NIBP patch 320 can extend the lifespan of the power source 328, allowing data to be collected over a period of time.

Figure 4B:
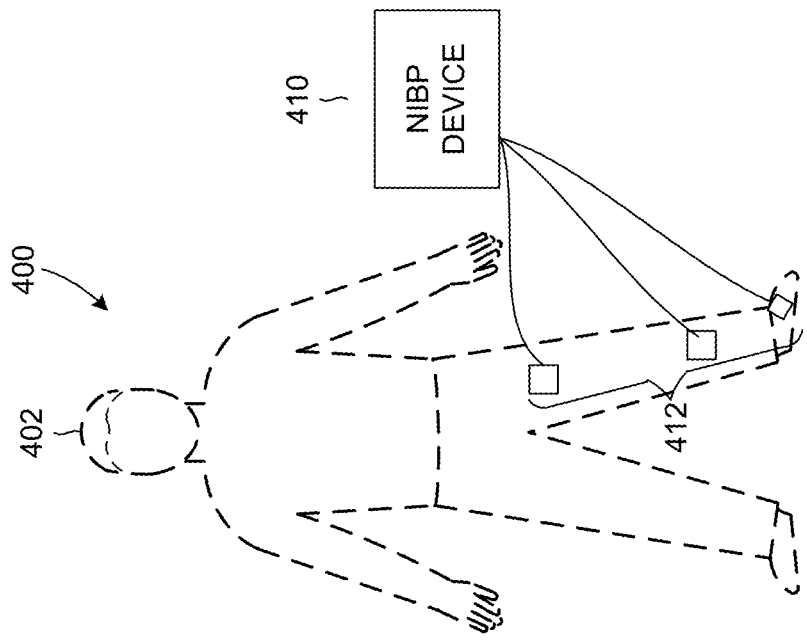
FIGS. 4A-4B are example NIBP monitoring systems.
Figure 4A:
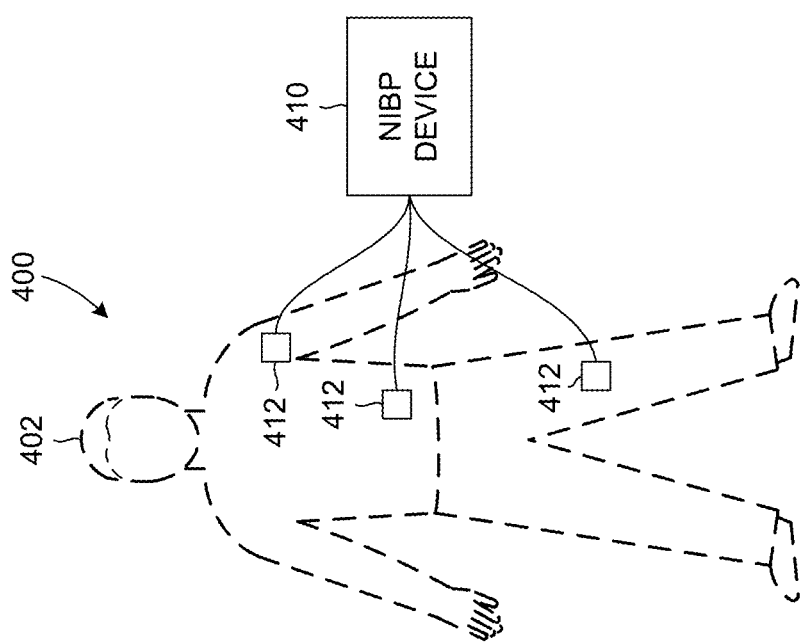

FIGS. 4A-4B illustrate example multi-site NIBP monitoring systems 400 that include an NIBP device 410 and NIBP sensors 412. The NIBP sensors 412 can be placed on a patient 402 to generate NIBP signals/data that can be processed by the NIBP device 410 to calculate a blood pressure and/or vessel dynamics of the patient 402. Multi-site blood pressure monitoring can include two or more NIBP sensors 412 that can be distributed and/or placed at various positions on the body of the patient 402. In FIG. 4A, the NIBP sensors 412 are dispersed across the body of the patient 402 for whole body blood pressure monitoring. In FIG. 4B, the NIBP sensors 412 are clustered or strategically placed around an area for local blood pressure monitoring, such as might be used in a surgery situation. The example shown in FIG. 4B could be used to monitor a diabetes patient for blood flow, blood pressure, and/or vessel dynamics in/through the patient's leg to improve the efficacy of diabetes treatment in the patient in both an emergency and non-emergency setting. Further, alternative arrangements could cluster multiple NIBP patches around a pregnant women's abdomen to measure blood pressure, blood flow, and/or vessel dynamics of the mother and fetus during pregnancy. Other example configurations are included and can be patient-specific and/or disease/infection/operating environment-specific, as needed.

Figure 5:
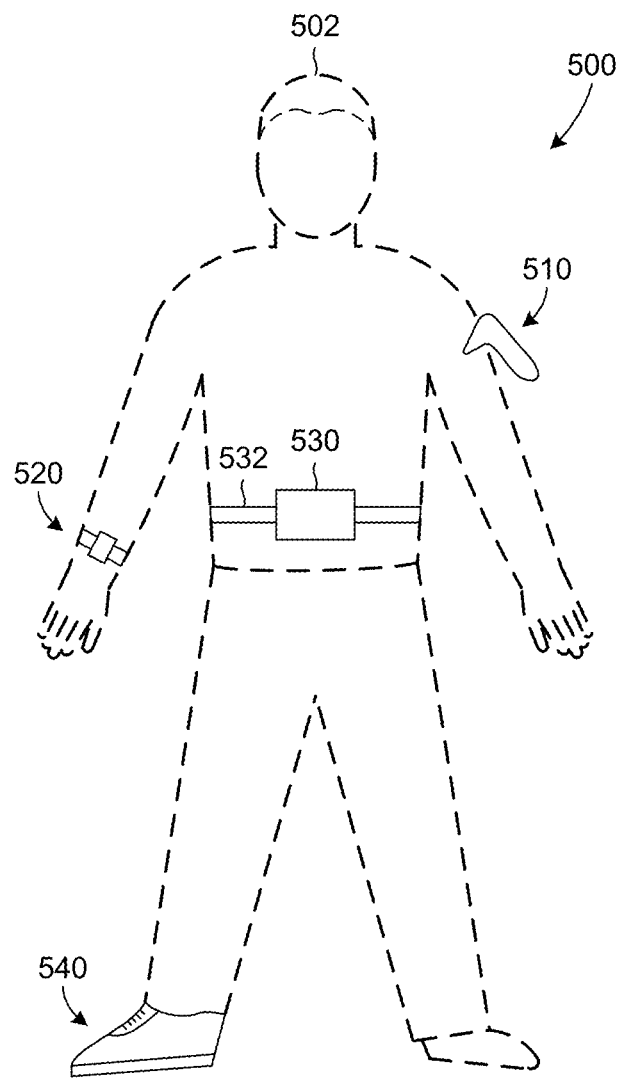
FIG. 5 is an example wearable and/or contactable NIBP system.

FIG. 5 illustrates an example wearable and/or contactable NIBP system 500. The system 500 includes a wearable and/or contactable NIBP device that can be placed on a patient 502 to monitor a blood pressure and/or vessel dynamics of the patient 502. Contactable NIBP devices can be placed against the skin of the patient 502 and wearable articles can secure the contactable NIBP devices so they are worn by the patient 502, such as for an extended period of time.

An example contactable device can include a handheld NIBP device 510 that a user, or other, can press against the skin of the patient 502 to calculate a blood pressure and/or vessel dynamics. The handheld NIBP device 510 can be held against the patient's skin to acquire the NIBP signal and/or data and can provide a notification to the user when such data has been collected and/or processed.

Example wearable articles with a NIBP device can include a watch 520, an NIBP device 530 on a belt 532, a shoe 540 and/or other wearable articles like vests and/or harnesses. In the example watch 520 and shoe 540, the NIBP device can be integrated into the wearable item and can include an NIBP sensor that contacts the skin of the patient 502 to generate the NIBP signal and/or data. The NIBP device 530 on a belt 532 can include a sensor that contacts the patient 502 to generate the NIBP signal and/or data. The wearable devices can be worn for extended period of times to monitor the blood pressure and/or vessel dynamics of the patient 502. The collected monitoring data can assist with patient 502 care and/or treatment. The NIBP devices 520, 530, 540 could be removable from their respective wearable article that then secures the NIBP device for contact against the patient.

Figure 6:
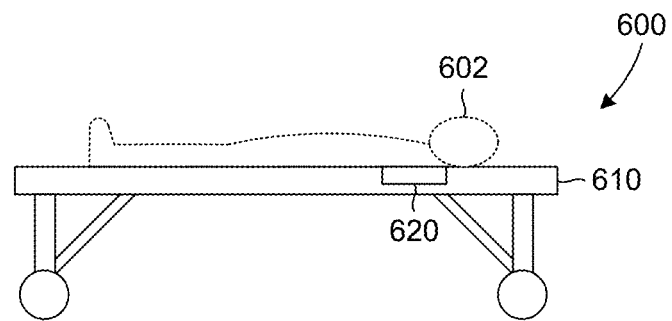
FIG. 6 is a further example contactable NIBP system.

FIG. 6 illustrates another contactable NIBP system 600 that includes an NIBP device 620 that is integrated with and/or placed in a patient bed/gurney 610. The NIBP device 620 includes a sensor that contacts a patient 602 that is lying in the patient bed 610, such as a hospital bed, gurney, cot, or other patient transport device. The sensor can generate an NIBP signal and/or data that can be processed to calculate a blood pressure and/or vessel dynamics of the patient 602. The contactable NIBP device 620 can be integrated in other objects and/or items that a patient 602 can come into contact with, such as patient injury support devices and/or other support structures. The integration of a contactable NIBP device can assist with monitoring and/or treating a patient based on the data collected and/or calculated by the NIBP device.

It will be appreciated that variants of the above-disclosed and other features and functions, or alternatives thereof, may be combined into many other different devices, systems and/or applications. Various presently unforeseen or unanticipated alternatives, modifications, variations, or improvements therein may be subsequently made by those skilled in the art, which are also intended to be encompassed by the following claims.

The invention claimed is:

1. A medical device, comprising:
   an emitter configured to emit electromagnetic waves, mechanical waves, or both the electromagnetic waves and the mechanical waves towards blood flowing through a blood vessel of a patient;
   a detector configured to:
      receive first reflected waves reflected from one or both of the blood vessel or surrounding tissue, the first reflected waves comprising first reflected electromagnetic waves, first reflected mechanical waves, or both the first reflected electromagnetic waves and the first reflected mechanical waves;
      receive second reflected waves reflected from the blood flowing through the blood vessel, the second reflected waves comprising second reflected electromagnetic waves, second reflected mechanical waves, or both the second reflected electromagnetic waves and the second reflected mechanical waves; and
      generate a signal based on one or both of the first reflected waves and the second reflected waves; and
   a processor configured to:
      determine an instantaneous blood velocity and a pulse wave velocity of the blood flowing through the blood vessel based on the signal; and
      determine a metric equal to a product of the instantaneous blood velocity, a density of the blood, and the pulse wave velocity;
      receive data indicative of cardiopulmonary resuscitation (CPR) being administered to the patient; and
      in response to receiving the data indicative of the CPR being administered to the patient, determine an efficacy of the CPR based on the metric.

2. The medical device of claim 1, wherein a patch comprises the emitter and the detector, the patch being configured to be attached to a neck or abdomen of the patient,
   wherein the blood vessel is located in the neck or abdomen of the patient.

3. The medical device of claim 1, wherein the emitter and the detector are comprised in a wearable article that is configured to be worn by the patient.

4. The medical device of claim 1, wherein the emitter and the detector are wirelessly coupled to the processor.

5. The medical device of claim 1, wherein the electromagnetic waves comprise light and the mechanical waves comprise ultrasound.

6. The medical device of claim 1, the instantaneous blood velocity being a first instantaneous blood velocity during a first cardiac cycle, the pulse wave velocity being a first pulse wave velocity during the first cardiac cycle, the metric being a first metric, wherein the processor is further configured to:
   determine, based on the signal, a second instantaneous blood velocity and a second pulse wave velocity during a second cardiac cycle;
   determine a second metric equal to a product of the second instantaneous blood velocity, the density of the blood, and the second pulse wave velocity; and
   determine a change between the first metric and the second metric,
   wherein determining the efficacy of the CPR comprises comparing the change to a threshold value.

7. The medical device of claim 1, wherein the medical device is further configured to transmit an indication of the efficacy of the CPR to an output device.

8. The medical device of claim 1, wherein the processor is further configured to generate an instruction to alter a characteristic of the CPR based on the determined efficacy of the CPR.

9. The medical device of claim 1, wherein the processor is further configured to generate a user instruction or prompt to administer a treatment to the patient based on the efficacy of the CPR.

10. The medical device of claim 1, further comprising:
    a vital sign module configured to detect a vital sign of the patient.

11. The medical device of claim 10, wherein the vital sign module is configured to detect the vital sign by generating ventilation data, oxygenation data, or electrocardiogram (ECG) data.

12. The medical device of claim 11, wherein the processor is further configured to:
    in response to receiving the data indicative that CPR is being administered, determine one or both of an efficacy of administered ventilations and an oxygenation state of the patient based on the metric and the vital sign data.

13. The medical device of claim 11, wherein the processor is further configured to:
    in response to receiving the data indicative of CPR being administered, determine whether the ECG data is indicative of hemodynamic collapse of the patient.

14. The medical device of claim 1, wherein the processor is further configured to determine blood vessel dynamics of the blood vessel based on the signal.

15. The medical device of claim 14, wherein the blood vessel dynamics comprise a blood rate, a blood delivery volume, or both the blood rate and the blood delivery volume, and
    wherein the processor is further configured to identify a low blood flow condition of the patient based on the blood rate, the blood delivery volume, or both the blood rate and the blood delivery volume.

16. The medical device of claim 15, wherein the processor is further configured to assign a severity score to the low blood flow condition, the severity score being indicative of an impact of the low blood flow condition on a physiological state of the patient.

17. A medical device, comprising:
a receiver configured to:
- receive reflected waves comprising electromagnetic waves, mechanical waves, or both electromagnetic waves and mechanical waves transmitted into a blood vessel and surrounding tissue of a patient during a cardiac cycle; and
- generate signals based on the received reflected waves;

a vital sign module configured to detect a vital sign of the patient; and
a processor configured to:
- determine, based on the signals, multiple instantaneous blood velocities of blood flowing through the blood vessel at different times during the cardiac cycle;
- determine, based on the signals, a pulse wave velocity of a pulse traveling along the blood vessel during the cardiac cycle;
- determine metrics equal to products of the instantaneous blood velocities, a density of blood, and the pulse wave velocity;
- receive data indicative of cardiopulmonary resuscitation (CPR) being administered to the patient;
- in response to receiving data indicative of CPR administration to the patient, determine an efficacy of the CPR based on the sensed vital sign of the patient and the metrics.

18. The medical device of claim 17, wherein the receiver is wirelessly coupled to the processing module.

19. The medical device of claim 17, wherein the medical device is configured to output an indication of the efficacy of the CPR.

20. The medical device of claim 17, wherein the processor is further configured to generate an instruction to alter a characteristic of the CPR based on the determined efficacy of the CPR.

21. The medical device of claim 20, wherein the characteristic of the CPR includes a compression depth, a compression rate, or a compression position.

22. The medical device of claim 17, wherein the processor is further configured to generate a user instruction or prompt to administer a treatment to the patient based on the metrics, the efficacy of the CPR, or both the metrics and the efficacy of the CPR.

23. The medical device of claim 17, wherein the processor is further configured to determine one or both of an efficacy of administered ventilations and an oxygenation state of the patient based on the metrics and the vital sign data.

24. The medical device of claim 17, wherein the vital sign module is configured to detect ECG data of the patient, and
wherein the processor is further configured to, in response to receiving the data indicative of the CPR being administered, to determine whether the ECG data is indicative of hemodynamic collapse of the patient.

* * * * *